United States Patent
Spoonamore

(10) Patent No.: US 8,021,427 B2
(45) Date of Patent: Sep. 20, 2011

(54) INTERVERTEBRAL DISK PROSTHESIS WITH ELASTOMERIC INSERT

(76) Inventor: Mark Spoonamore, Los Angeles, CA (US)

( * ) Notice: Subject to any disclaimer, the term of this patent is extended or adjusted under 35 U.S.C. 154(b) by 0 days.

(21) Appl. No.: 12/838,374

(22) Filed: Jul. 16, 2010

(65) Prior Publication Data

US 2011/0071638 A1    Mar. 24, 2011

Related U.S. Application Data

(63) Continuation of application No. 10/641,666, filed on Aug. 14, 2003.

(51) Int. Cl.
A61F 2/44        (2006.01)
(52) U.S. Cl. .................. 623/17.14; 623/17.15
(58) Field of Classification Search ............... 623/17.14, 623/17.15, 17.13
See application file for complete search history.

(56) References Cited

U.S. PATENT DOCUMENTS

| | | | |
|---|---|---|---|
| 3,605,123 A | 9/1971 | Hahn | |
| 4,542,539 A | 9/1985 | Rowe, Jr. et al. | |
| 4,743,256 A | 5/1988 | Brantigan | |
| 4,756,862 A | 7/1988 | Spector et al. | |
| 5,071,437 A | 12/1991 | Steffee | |
| 5,171,281 A | 12/1992 | Parsons et al. | |
| 5,258,031 A | 11/1993 | Salib et al. | |
| 5,306,309 A | 4/1994 | Wagner et al. | |
| 5,314,477 A | 5/1994 | Marnay | |
| 5,401,269 A | 3/1995 | Buttner-Janz et al. | |
| 5,425,773 A | 6/1995 | Boyd et al. | |
| 5,507,816 A | 4/1996 | Bullivant | |
| 5,556,431 A | 9/1996 | Buttner-Janz | |
| 5,562,738 A | 10/1996 | Boyd et al. | |
| 5,571,190 A | 11/1996 | Ulrich et al. | |
| 5,676,701 A | 10/1997 | Yuan et al. | |
| 5,893,889 A | 4/1999 | Harrington | |
| 5,895,428 A | 4/1999 | Berry | |
| 5,899,941 A | 5/1999 | Nishijima et al. | |
| 6,193,761 B1 | 2/2001 | Treacy | |
| 6,368,350 B1 | 4/2002 | Erickson et al. | |
| 6,371,985 B1 | 4/2002 | Goldberg | |
| 6,440,168 B1 | 8/2002 | Cauthen | |
| 6,471,725 B1 | 10/2002 | Ralph et al. | |
| 2002/0128715 A1 | 9/2002 | Bryan et al. | |
| 2003/0120347 A1 * | 6/2003 | Steinberg | 623/17.13 |
| 2004/0193273 A1 | 9/2004 | Huang | |

FOREIGN PATENT DOCUMENTS

| | | |
|---|---|---|
| EP | 599419 A2 | 6/1994 |
| JP | 07289562 A | 11/1995 |
| JP | 10501705 | 2/1998 |
| JP | 10071157 | 3/1998 |
| JP | 11506658 | 6/1999 |
| WO | WO 94/04100 A1 | 3/1994 |

OTHER PUBLICATIONS

Japanese Application No. 2006-523222—Notice of Grant.
Japanese Application No. 2006-523222—Allowed Claims (translation).
Japanese Application No. 2006-523222—Office Action (with translation).

* cited by examiner

*Primary Examiner* — Brian E. Pellegrino
(74) *Attorney, Agent, or Firm* — Mark H. Krietzman; Baker & Hostetler, LLP

(57) ABSTRACT

Described herein is an intervertebral disk prosthesis with an angled leading edge for insertion into the Intervertebral space. The disk prosthesis may provide for both rotation and compression.

5 Claims, 4 Drawing Sheets

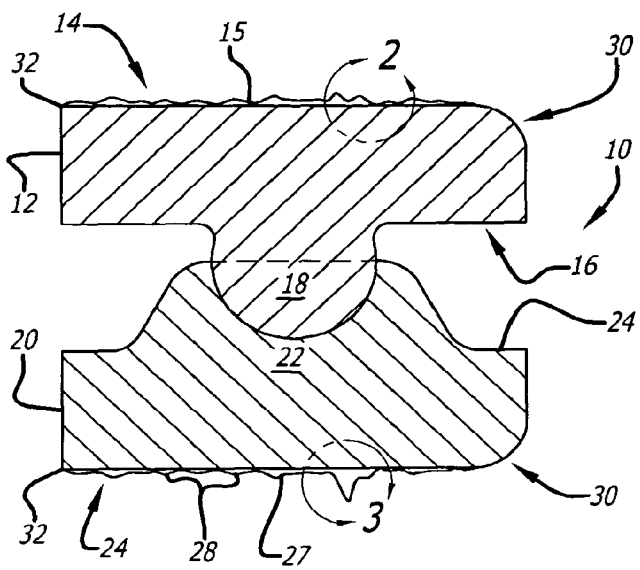
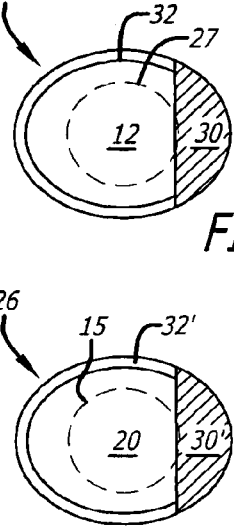
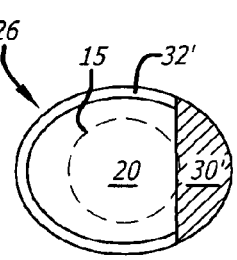
FIG. 1A
FIG. 1B
FIG. 1C
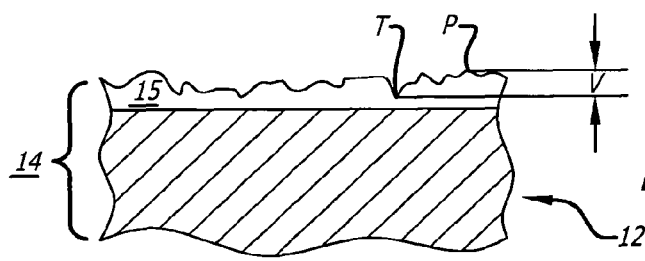
FIG. 2
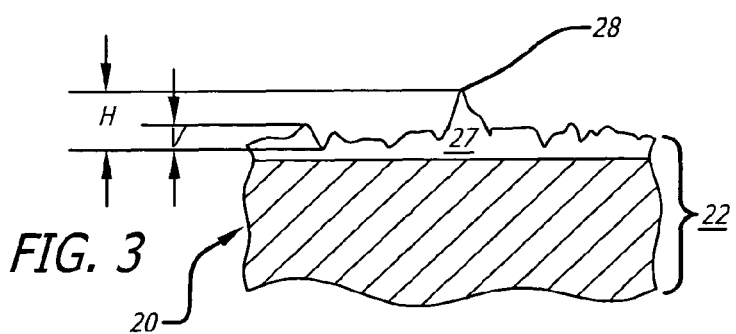
FIG. 3

INTERVERTEBRAL DISK PROSTHESIS WITH ELASTOMERIC INSERT

The instant application claims priority to, and is a continuation of, U.S. application Ser. No. 10/641,666, filed on Aug. 14, 2003.

BACKGROUND OF THE INVENTION

1. Field of the Invention

A method and device to stabilize an intervertebral space. More particularly an artificial spinal disk and method of installation and stabilization.

2. Description of Related Art

Diseased or degenerated disk material between vertebrae can cause persistent pain, stiffness and health problems. Surgical techniques such as fusion of two adjacent vertebrae can stabilize the spinal column but trade mobility for the support.

Artificial or prosthetic disk devices are known in the art. Primarily there are two types of solutions: an elastic type insert see generally U.S. Pat. No. 5,171,280; and a ball and socket type insert.

Elastic type inserts tend to degenerate and wear out over time. Moreover, elastic type inserts may become dislodged from the disk space. Ball and socket inserts allow for some mobility, and often perform well in vitro. However, in vivo, a ball and socket which performed well in the lab may not provide the same mobility as shown in vitro. U.S. Pat. No. 6,368,350 describes a ball and socket type disk replacement which is offset and has a variable access of rotation to mimic the movement of the spinal column.

Absent from the prior art is a ball and socket intervertebral disk replacement (prosthesis) which allows for rotation and compression.

Insertion into the intervertebral space of an intervertebral disk replacement is also a challenge. Methods of prosthetic disk insertion normally require intervertebral spacers to retract the upper and lower vertebrae and open up the space between those vertebrae and then to insert the disk replacement into the intervertebral space. During surgery, using intervertebral spacers requires additional time and bears with it the risk of the spinal column being damaged by the insertion of spacers. Other risks include opening the intervertebral space beyond what is necessary. It would therefore be a desideratum to have a method for fitting a disk replacement into a spinal column which could open the intervertebral space during insertion of the disk replacement. It would also be a desideratum to have a ball and socket disk prosthesis which provides for rotation and compression.

SUMMARY OF THE INVENTION

According to one aspect of the invention the ball and socket intervertebral disk replacement provides both rotation and compression.

In another aspect the intervertebral disk replacement can be used to help open up the intervertebral space. The leading edge of the IVDR helps retract the upper and lower vertebrae, relative to the intervertebral space being opened up.

BRIEF DESCRIPTION OF THE DRAWINGS

FIG. 1A shows a cut-away side view of an intervertebral disk replacement.

FIG. 1B shows a top-view of the embodiment showing shown in FIG. 1A.

FIG. 1C shows the bottom-view of the embodiment shown in FIG. 1A.

FIG. 2 shows an exploded partial view of the ball half of the intervertebral disk replacement of FIG. 1A.

FIG. 3 shows a blown-up partial view of the socket half of the intervertebral disk replacement of FIG. 1A.

Figure 4:
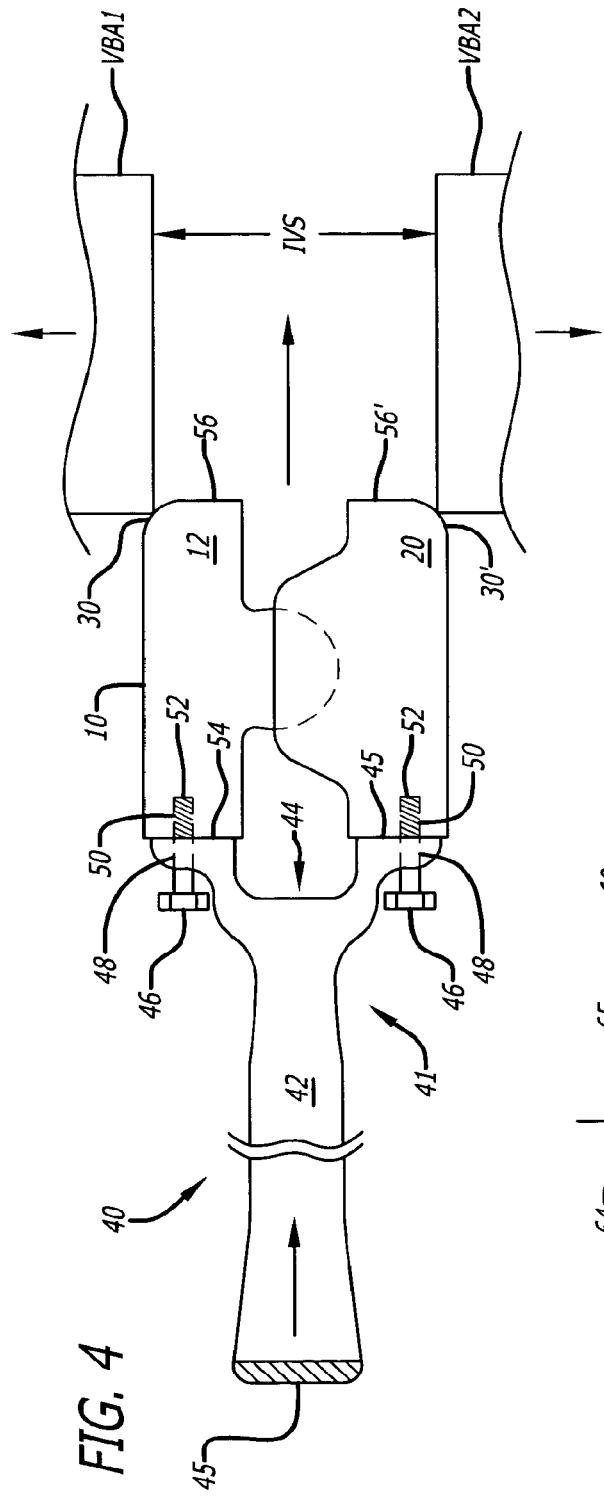
FIG. 4 shows an assembly view of the insertion of an intervertebral disk replacement.

It should be appreciated that for simplicity and clarity of illustration, elements shown in the Figures have not necessarily been drawn to scale. For example, the dimensions of some of the elements are exaggerated relative to each other for clarity. Further, where considered appropriate, reference numerals have been repeated among the Figures to indicate corresponding elements.

Other features and advantages of the present invention will be set forth, in part, in the descriptions which follow and the accompanying drawings, wherein the preferred embodiments of the present invention are described and shown, and in part, will become apparent to those skilled in the art upon examination of the following detailed description taken in conjunction with the accompanying drawings or may be learned by practice of the present invention. The advantages of the present invention may be realized and attained by means of the instrumentalities and combinations particularly pointed out in the appended claims.

DETAILED DESCRIPTION OF THE INVENTION

An intervertebral disk replacement "IVDR" is shown in FIG. 1A through 1C. The IVDR 10 is comprised of two halves, each half is a referred to generally as a base. The ball half base 12, has a vertebra interface surface 14 which may have a rough principal surface or a porous principal surface 15 or both a rough and porous principal surface. Opposite the vertebra interface surface 14 is a bottom surface 16 and extending therefrom is a ball head 18.

Also shown is the socket half base 20 which supports a ball receiving socket 22 extended from its interior surface 24. The ball receiving socket 22 is of a size and shape to receive and hold the ball head 18.

Opposite the ball receiving socket 22 is the vertebra interface surface 26 of the socket half 20 of the IVDR 10. This vertebra interface surface 26 also has a principal surface 27 which may be rough, porous and/or porous and rough. Moreover, protrusion 28 may extend from the principal surface 27. The number of protrusions is variable and about two to about twenty protrusions are preferred, with about three to about twelve protrusions being more preferred and about three to about six protrusions being most preferred. Although protrusion 28 are shown only extending from the principal surface 26 of the socket half base 20 protrusions can also be formed on, or extended from, the principal surface 15 of the ball half base 12. A section of each vertebra interface surfaces 14 and 26 (shown in FIGS. 1B and 1C) is angled to form a retracting edge 30 and 30'. The retracting edges 30 and 30' are distinguishable from a radius edges 32 and 32'. The radius edges 32 and 32' are about equal distance from center of each vertebral interface surface 14 and 26.

FIG. 2 shows a blown-up view of a portion of the principal surface 15 of the ball half base 12. One measure of the roughness of the principal surface is the variance "V". The variance "V" is a measure of the distance between the highest peak "P" and the lowest trough "T" on the principal surface 15.

FIG. 3 illustrates one or more protrusions extending from the principal surface 15. The protrusion 28 have a height "H" greater even than the variance "V".

Preferred materials for the construction of the IVDR include chrome cobalt, and titanium. It is possible to control the porosity at the principal surfaces 15 and 27 by either selection of material with the appropriate porosity or by modifying the principal surface to increase or decrease porosity. Well known in the art are methods such as shoot peening or ion beam exposure which can be used to modify the porosity of a principal surface. Porosity of the principle surface can facilitate bone growth from the adjacent vertebra to the principal surface of the IVDR.

Moreover, it is possible to coat the principal surfaces 15 and 27 (not shown) by commonly used methods such as sintering, pressure sintering (to add metal), cold spray, or coating with porous beads whereby a plastic or other material is affixed to the principal surfaces. The methods for affixing or applying coating materials to the base substrate materials for the IVDR 10 are commonly known in the art by those skilled in the art and therefore a detailed description of those processes are not provided. However, it is possible that after application of a coating (not shown) it may be advantageous to further sinter, or otherwise effect the coating to further select the roughness, variance, and/or porosity of the coating material.

The angular leading edge of each IVDR forms a retracting edge 30 and 30' useful for insertion of the IVDR into the spinal column. Generally accepted practices of disk replacement require the opening of the intervertebral space "IVS" before insertion of an IVDR. FIG. 4 shows the insertion of the IVDR 10 into the IVS. For insertion, the IVDR 10 is attached to the IVDR tool 41. The IVDR tool 41 is comprised of a handle at one end a head 44 and a force receiving tail 45. The IVDR 10 can be attached to the IVDR tool 41 with bolts 46 which extend through guide 48 in the head 44. The bolt 46 extends through the guide 48 and into bolt receiving channels 50 at the anterior surface 54 of the IVDR 10. When firmly attached to the IVDR 10, the IVDR tool 41 is positioned to orient the posterior edges 56 and 56' of the IVDR 10 with the IVS between an upper and lower vertebra "DVA1" and "DVA2". To effectuate installation of the IVDR 10 force is applied at the force receiving tail 45 of the IVDR tool 41. As the force is applied to the IVDR tool 41 the posterior edges 56 and 56' of the IVDR 10, which is also the location of the retracting edges 30 and 30' slide into the IVS. The retracting edges 30 and 30' (formed by the angular leading edges) wedged into the IVS and open the IVS up to accept the installation of the IVDR 10. It is also possible and may be desirable to first partially retract the IVS with spacers and then insert the retracting edges 30 and 30'. It is also possible and may be desirable to first partially retract the IVS with spacers and then insert the retracting edges 30 and 30'.

Once the IVDR is positioned in the IVS bone from the upper and lower vertebra VDA1 and VDA2 may grow into the principle surfaces 15 and 27 of the IVDR 10. Bone growth into a porous or rough region is not wholly predictable, therefore the roughness of the principal surfaces 15 and 27 and/or the protrusion 28 can be useful to provide additional anchor points between the IVDR 10 and the upper and/or lower vertebra VDA1 and VDA2.

Figure 5:
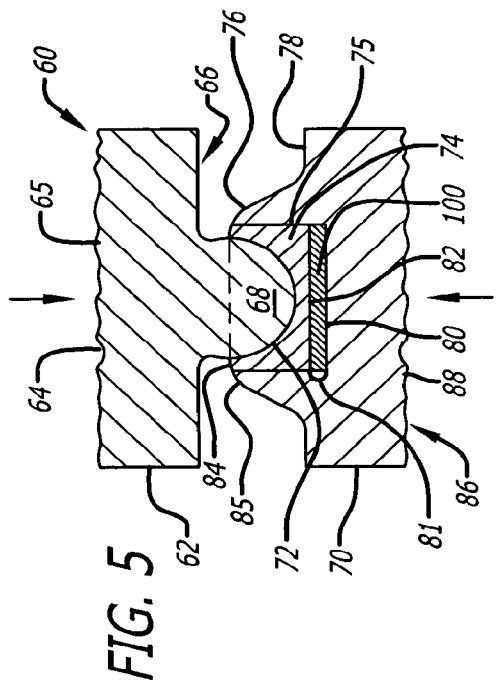
FIG. 5 shows a compressible ball and socket intervertebral disk replacement.

One limitation of prior art ball and socket vertebral disk replacement prosthetic devices is an inability to mimic the compression of a natural disk. The embodiment shown in FIG. 5 is a ball and socket IVDR 60 with a compressing function. The compressing function is important to mimic the action of a natural vertebra. A compressing function acts as a shock absorber. The embodiment shown in FIG. 5 is able to simultaneously flex and compress, or to compress and extend. A simple ball and socket disk replacement allows some extension and flexion motion, as opposed to a fusion of vertebra, however, the simple ball and socket motion is without the shock absorbing quality that a natural disk can provide.

In this embodiment the ball half base 62 of the IVDR 60, is substantially similar to the ball half base 12 of the IVDR shown in FIG. 1A. The ball half base 62 has a vertebra interface surface with a porous and/or rough principle surface 65 a bottom surface 66 and a ball head 68 extending from the bottom surface 66. The socket half base 70 of the IVDR 60 has a moveable ball receiving socket 72 supported on a body 74 in a socket guide channel 75. The ball receiving socket is of the size and shape to receive the ball's head 68. The socket guide channel 75 is surrounded by an extended socket support rim 76 which extends from the interior surface 78 of the socket half base 70 of the IVDR 60. An elastomeric insert 100 fits at the bottom 80 of the socket guide channel 75 and the bottom 82 of the body 74. In an elastomeric insert containing region 81. Containing the elastomeric insert 100 beneath the body 74 of the ball receiving socket 72 is not intended as a limitation. Those skilled in the art will recognize that an elastomeric material 100 may be contained in the ball half base and/or the socket half base of an IVDR.

Suitable elastomeric inserts include, but are not limited to C-Flex™ (Concept Inc.) or Pellethane™ (DOW Chemical), styrene-butadiene-butylene-styrene copolymer (SBBS), styrene-butadiene-styrene copolymer (SBS).

The top edge of the ball receiving socket 84 is shown in line with the top edge 85 of the socket support rim 76. The socket half base 70 of the IVDR 60 also has a top vertebra interfaced surface 86 which has a principle surface region 88. When a compression force "F" is applied the elastomeric insert 100 can compress. During compression (FIG. 6B) the top edge 79 of the ball receiving socket 72 can then move to a position below the top edge 85 of the socket support rim 76 of the socket guide channel 75. It will be apparent to those skilled in the art that the movable ball receiving socket may be switched for a movable ball head sitting within a guide in the ball half base 62 of the IVDR 60. It should also be apparent to those skilled in the art that both the ball receiving socket and the ball head portions of an IVDR may be placed in guides with elastomeric inserts at the base thereof and used in cooperation to provide a compression function.

EXAMPLE

The following example is given to enable those skilled in the art to most clearly understand and to practice the present invention which is not to be considered as limiting the scope of the invention but merely as being illustrative and representative thereof.

Example 1

Figure 6A:
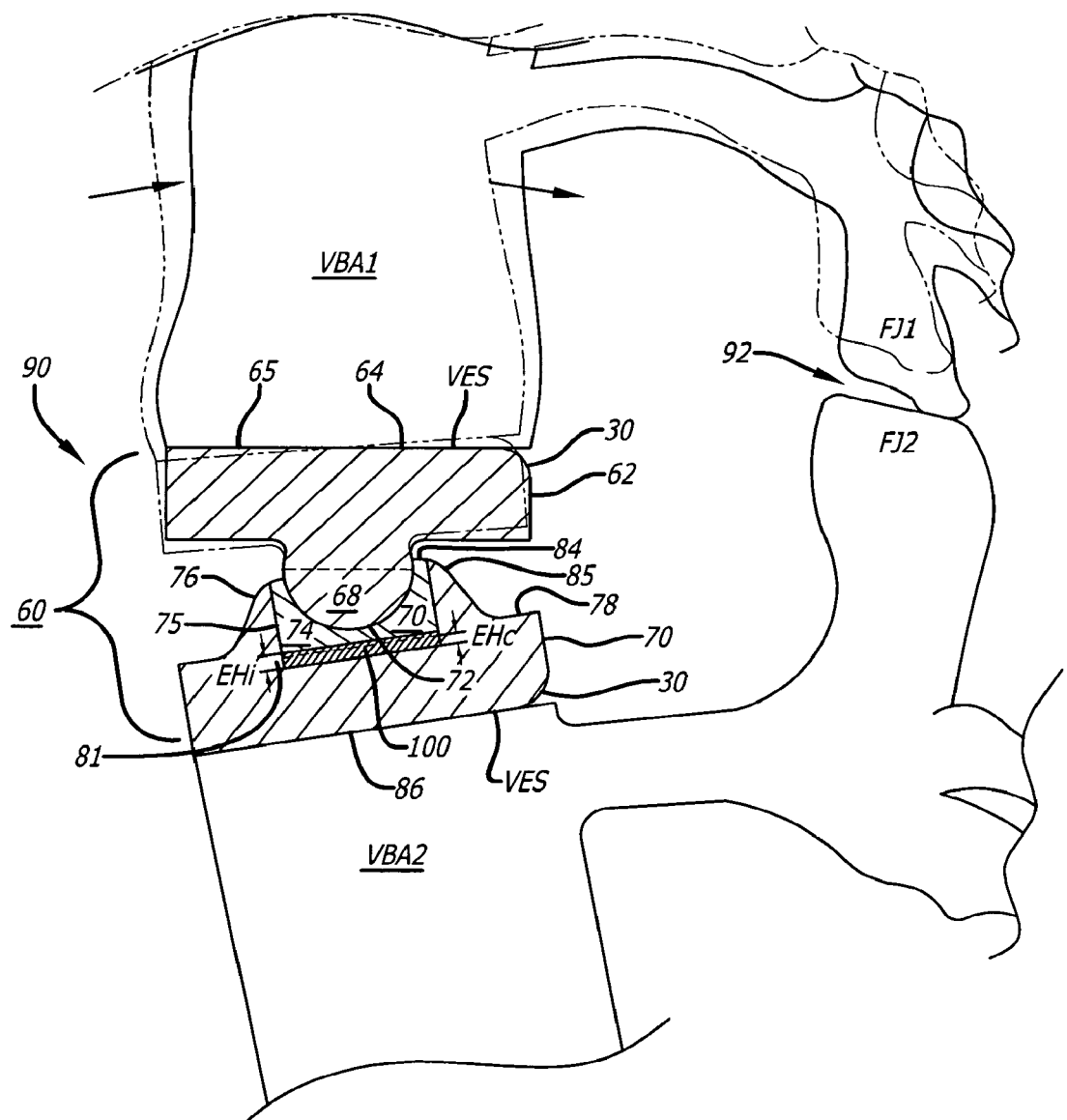
FIGS. 6A and 6B show a cut-away side view depicting the function of the intervertebral disk replacement, in situ, with the subject bending backwards.

Shown in FIG. 6A is the IVDR 60 of FIG. 5 in vivo. The IVDR 60 is placed between an upper vertebra VDA1 and a lower vertebra VDA2. The vertebra interface surfaces 64 and 81 are against the vertebra exterior surfaces "VES". In vivo, the upper vertebra VDA1 and the lower vertebra VDA2 each has an interface extending there from FJ1 and FJ2 respectively. The sub-joints FJ1 and FJ2 meet at the sub-joint interface 92. The sub-joints FJ1 and FJ2 at the interface "lock out" and restrict rotation of the upper and lower vertebra around the IVDR 60. Traditional ball and socket inter-vertebral disk replacement devices are unable to move further when the facet joints (illustrated in FIGS. 6A and 6B as the sub-joints FJ1 and FJ2) meet at the subjoint interface 92.

Figure 6B:
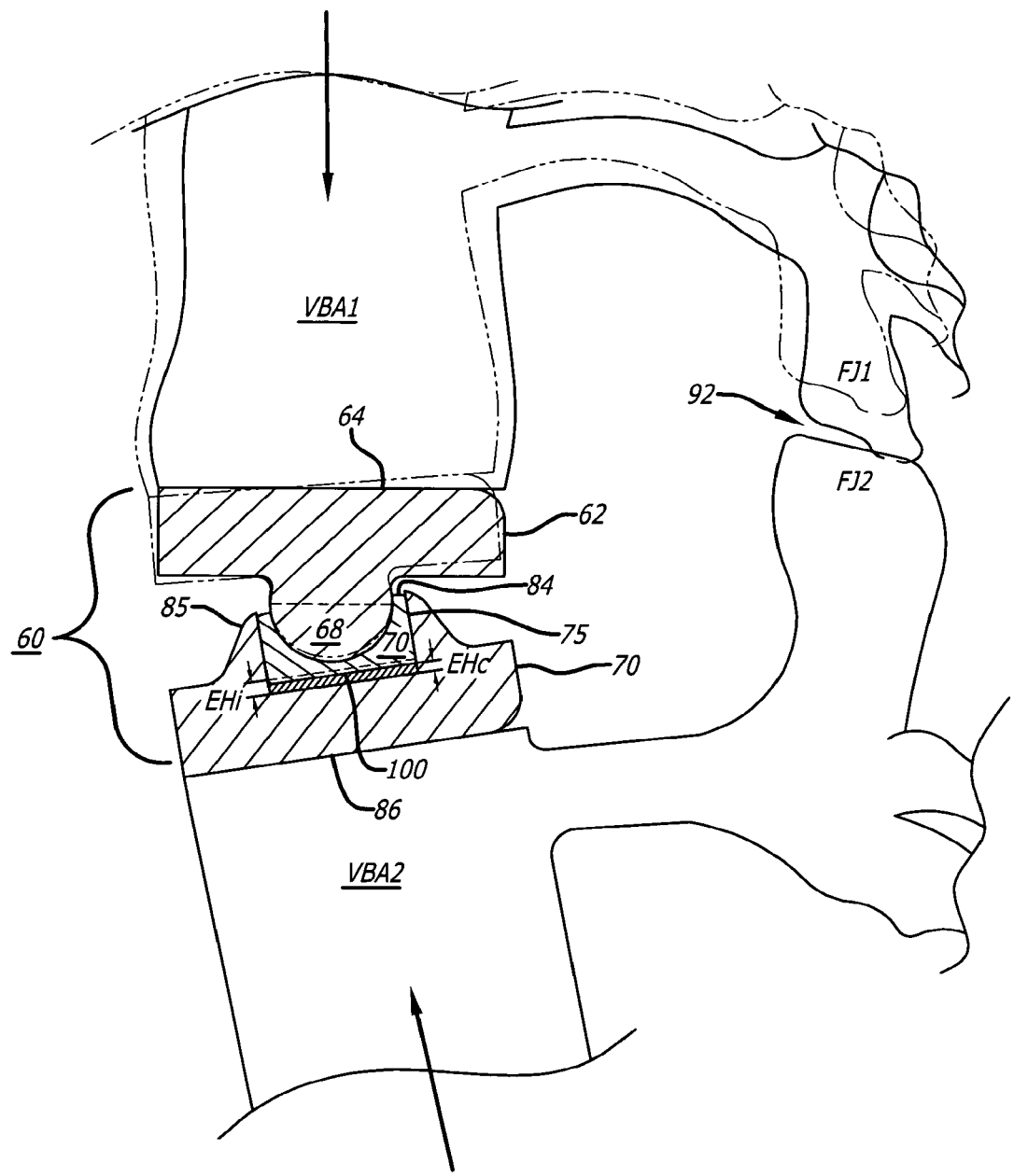

The distance between the bottom of the socket guide channel 80 and the bottom 82 of the ball receiving socket 82 is defined by the elastomeric material 100 as the initial elastomeric height $EH_i$. After the facet joints have interface and "locked out" at the subjoint interface 92, as shown in FIG. 6B, the movable ball receiving socket 72 has further movement, via the compression of the elastomeric material 100, as shown by the reduction in the initial elastomeric height "$EH_I$" compared to the compressed elastomeric material 100 height "$EH_C$".

The compression of the elastomeric material 100, although shown substantially even, may also be localized whereby one area of the elastomeric material 100 compresses greater than another area thereby providing additional flex or extension. In those embodiments which provide uneven compression, to facilitate the uneven compression of the elastomeric material 100 the movable ball receiving socket 72 should have a diameter which is less than the diameter of the socket guide channel 75 to allow for uneven movement within the socket guide channel 75.

Figure 7:
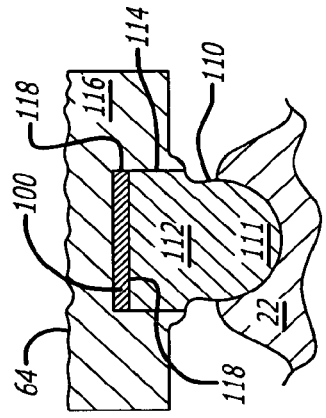
FIG. 7 shows a partial view of a movable ball half base.

FIG. 7 shows a moveable ball 110 with a ball head 111 on a ball body 112 within a ball guide channel 114 formed in ball half base 116. An elastomeric insert 100 to provide a compression function is positioned at the bottom 118 of the moveable ball body 112. The ball head 111 fits into a socket 22. A vertebra interface surface 64 is formed on the ball half base 116.

Since certain changes may be made in the above apparatus without departing from the scope of the invention herein involved, it is intended that all matter contained in the above description, as shown in the accompanying drawing, shall be interpreted in an illustrative, and not a limiting sense. It is not intended that the invention be limited to the illustrative embodiments.

I claim:

1. A two half intervertebral disk prosthesis comprising:
    a socket half base with a vertebra interface surface on one side;
    a socket guide formed in the side of the socket half base opposite the vertebra interface surface;
    a ball receiving socket moveable in the socket guide;
    an elastomeric insert between the bottom of the socket guide and the ball receiving socket;
    a ball half base with a vertebra interface surface on one side; and
    a ball head extending from the ball half base defining a neck and a spherical head, which mates into the ball receiving socket opposite the vertebra interface surface,
    further comprising an angular leading edge on at least one of socket half base and the ball half base; and wherein the elastomeric insert between the bottom of the socket guide and the ball receiving socket is shielded from direct impact by the ball half base.

2. The disk prosthesis of claim 1 further comprising a porous principal surface on at least one vertebra interface surface of the socket half base and the ball half base.

3. The disk prosthesis of claim 2 further comprising a coating on at least one principal surface.

4. The disk prosthesis of claim 1 further comprising a rough principal surface on at least one vertebra interface surface of the socket half base and the ball half base.

5. The disk prosthesis of claim 1 further comprising one or more protrusions on at least one vertebra interface surface of the socket half base and the ball half base.

* * * * *